US010352922B2

United States Patent
Reeber et al.

(10) Patent No.: US 10,352,922 B2
(45) Date of Patent: Jul. 16, 2019

(54) SYSTEM AND METHOD OF MEASURING HEMATOCRIT

(71) Applicant: Thermo Finnigan LLC, San Jose, CA (US)

(72) Inventors: Steven L. Reeber, San Jose, CA (US); John Glazier, San Jose, CA (US)

(73) Assignee: THERMO FINNIGAN LLC, San Jose, CA (US)

( * ) Notice: Subject to any disclaimer, the term of this patent is extended or adjusted under 35 U.S.C. 154(b) by 123 days.

(21) Appl. No.: 15/678,578

(22) Filed: Aug. 16, 2017

(65) Prior Publication Data

US 2019/0056378 A1 Feb. 21, 2019

(51) Int. Cl.
*G01N 33/49* (2006.01)
*G01N 21/47* (2006.01)
(Continued)

(52) U.S. Cl.
CPC ......... *G01N 33/49* (2013.01); *G01N 15/0606* (2013.01); *G01N 21/314* (2013.01); *G01N 21/4738* (2013.01); *G01N 21/8483* (2013.01); *G01N 33/523* (2013.01); *G01N 2015/0073* (2013.01); *G01N 2015/0693* (2013.01);
(Continued)

(58) Field of Classification Search
CPC .............. G01N 33/49; G01N 15/0606; G01N 21/4738; G01N 21/314; G01N 21/8483; G01N 33/523; G01N 2021/4754; G01N 2201/062; G01N 2201/06113;
(Continued)

(56) References Cited

U.S. PATENT DOCUMENTS

| 6,887,426 B2 | 5/2005 | Phillips et al. | |
| 7,426,407 B2 * | 9/2008 | Higgins | A61B 5/0075 600/322 |
| 2002/0165439 A1 * | 11/2002 | Schmitt | A61B 5/0059 600/309 |

FOREIGN PATENT DOCUMENTS

WO 2011097343 A1 8/2011

OTHER PUBLICATIONS

Capiau et al., "A Novel, Nondestructive, Dried Blood Spot-Based Hematocrit Prediction Method Using Noncontact Diffuse ReflectanceSpectroscopy," Anal. Chem., XP055337859, ISSN: 0003-2700, DOI: 10.1021/acs.analchem.6b01321, 9 pgs., 2016.

(Continued)

*Primary Examiner* — Jennifer Wecker
(74) *Attorney, Agent, or Firm* — A. J. Gokcek

(57) ABSTRACT

A system for measuring hematocrit in a whole blood sample is provided. An absorbent substrate is adapted to receive a whole blood sample. At least one light source is positioned to illuminate the sample on the substrate at first and second wavelengths. The first and second wavelengths are different from each other. A spectral sensor is positioned to measure a first intensity and a second intensity of light diffusely reflected from the sample at the first and second wavelengths, respectively. The diffusely reflected first and second intensities of light are compared to reference values to generate first and second reflectance values. A controller, coupled to the spectral sensor, is configured to determine a first differential reflectance between the first and second reflectances. The hematocrit level of the sample is determined based on a first stored relationship between hematocrit and a differential reflectance corresponding to the first and second wavelengths.

16 Claims, 8 Drawing Sheets

(51) Int. Cl.
  *G01N 21/31* (2006.01)
  *G01N 15/06* (2006.01)
  *G01N 33/52* (2006.01)
  *G01N 15/00* (2006.01)
  *G01N 21/84* (2006.01)
(52) U.S. Cl.
  CPC ............... *G01N 2021/4754* (2013.01); *G01N 2021/4769* (2013.01); *G01N 2201/062* (2013.01); *G01N 2201/06113* (2013.01)
(58) Field of Classification Search
  CPC ... G01N 2015/0693; G01N 2015/0703; G01N 2021/4769
  See application file for complete search history.

(56) References Cited

OTHER PUBLICATIONS

Miller IV et al., "An On-card Approach for Assessment of Hematocrit on Dried Blood Spots which Allows for Correction of Sample Volume," J. Anal. Bioanal. Techniques, 8 pgs, 2013.

\* cited by examiner

SYSTEM AND METHOD OF MEASURING HEMATOCRIT

FIELD OF THE INVENTION

This invention relates to measurement of hematocrit in a whole blood sample. More specifically, this invention relates to a differential reflectance measurement of hematocrit at two or more wavelengths for a whole blood spot on an absorbent medium.

BACKGROUND OF THE INVENTION

Hematocrit, which is the fraction of blood volume consisting of red blood cells, is a critical measurement for many blood-based clinical analytical applications. Existing hematocrit measurement techniques are primarily focused on noninvasive in vivo blood analysis or the in vitro analysis of liquid blood. These techniques for hematocrit measurement have incorporated various methods, including optical measurements (transmission or reflectance), centrifugation, and electrical measurements (e.g., conductivity) for the analysis of liquid blood in the body, extracorporeal channels, or cuvettes. They are often slow or hard to automate, and not generally applicable to the expanding field of blood spot analysis.

SUMMARY

Embodiments of the present invention disclose system and methods for measuring hematocrit in a whole blood sample. In one embodiment, a system for measuring hematocrit in a whole blood sample deposited on an absorbent substrate is provided. The system also includes at least one light source positioned to illuminate the blood sample on the substrate at first and second wavelengths. The first and second wavelengths are different from each other and fall in the range of 400 nm to 700 nm. The system further includes a spectral sensor positioned to measure a first intensity and a second intensity of light diffusely reflected from the blood sample at the first and second wavelengths, respectively. The diffusely reflected first and second intensities of light are compared to reference values to generate first and second reflectance values. The system also includes a controller, coupled to the spectral sensor, configured to (i) calculate first and second reflectances from the measured first and second intensities of diffusely reflected light by comparing the first and second intensities to reference values, (ii) determine a first differential reflectance between the first and second reflectances, and (iii) determine the hematocrit level of the whole blood sample based on a first stored relationship between hematocrit level and first differential reflectance corresponding to the first and second wavelengths.

In one embodiment, the at least one light source is further configured to illuminate the blood sample at a third wavelength different from the first and second wavelengths. The third wavelength falls within the range of 400 nm to 700 nm. The spectral sensor is configured to measure a third intensity of light diffusely reflected from the blood sample at the third wavelength. The diffusely reflected third intensity of light is converted to a third reflectance value. The controller is configured to determine a second differential reflectance between the third reflectance and a selected one of the first and second reflectances. The hematocrit level is determined based on one or both of the first stored relationship and a second stored relationship between hematocrit level and a differential reflectance corresponding to the third wavelength and the selected one of the first and second wavelengths.

The system may further comprise a light collector which transmits light from the at least one light source to the blood sample and receives and directs light diffusely reflected from the blood sample to the spectral sensor. In one embodiment, the light collector is an optical fiber probe having multiple fibers. A first portion of the fibers is coupled to the light source and a second portion of the fibers—different from the first portion—is coupled to the spectral sensor. In another embodiment, the light collector is mounted at an acute angle to the surface of the substrate.

The light sources may comprise, but are not limited to, one or more of the following: light emitting diode (LED) sources, incandescent lamps, discharge lamps or combinations thereof.

A housing and a holder may be provided for the substrate contained within the housing.

The absorbent substrate may comprise, but is not limited to, paper.

In one embodiment, the first wavelength and the second wavelength fall in the range of 505 nm to 590 nm.

In one embodiment, the first wavelength, the second wavelength, and the third wavelength fall in the range of 505 nm to 590 nm.

In another embodiment, a method of measuring hematocrit in a whole blood sample is provided. The method includes dispensing a whole blood sample on an absorbent medium and illuminating the sample at first and second wavelengths. The first and second wavelengths are different from each other and fall in the range of 400 nm to 700 nm. The method also includes measuring first and second intensities of light diffusely reflected from the blood sample at the first and second wavelengths, respectively. The diffusely reflected first and second intensities of light are compared to reference values to generate first and second reflectance values. The method further includes determining a first differential reflectance between the first and second reflectances, and determining the hematocrit level of the whole blood sample based on a first stored relationship between hematocrit level and first differential reflectance corresponding to the first and second wavelengths.

DETAILED DESCRIPTION OF EMBODIMENTS

Figure 1:
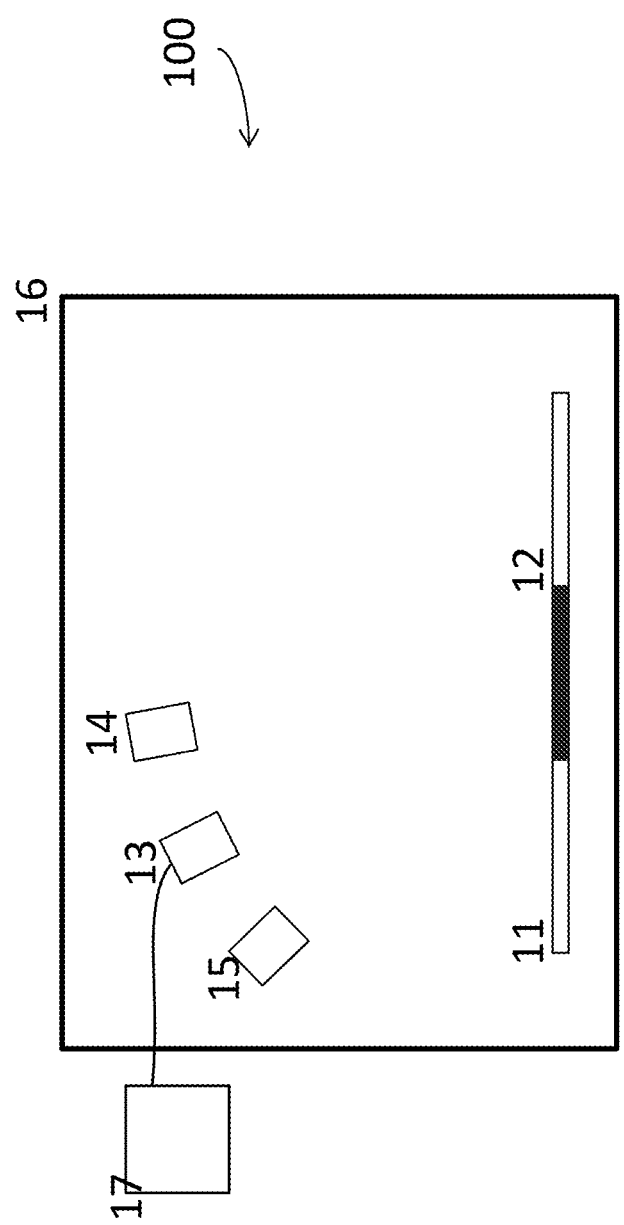
FIG. 1 is a block diagram of a system for measuring hematocrit in a whole blood sample, in accordance with one embodiment of the present invention.

FIG. 1 is a block diagram of a system 100 for measuring hematocrit in a whole blood sample 12 deposited on an absorbent substrate 11, in accordance with one embodiment of the present invention. The system 100 includes a spectral sensor 13, light source 14, an additional light source 15, which is optional, an enclosure 16, and a controller 17.

Figure 5:
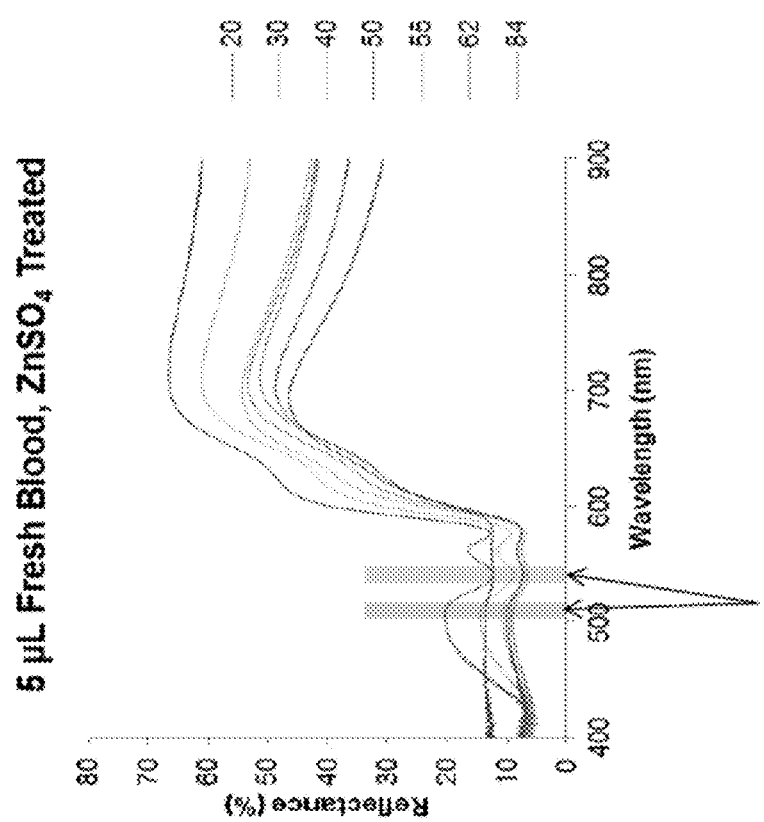
FIG. 5 shows reflectance spectra for 5 µL fresh whole blood at various levels of hematocrit, produced according to the process shown in FIG. 4.

The substrate 11 includes an absorbent material such as filter paper onto which a sample consisting of a defined volume—typically between 5-10 microliters—of whole blood is deposited, for example by pipetting. Other volumes of the sample can also be used. The whole blood sample 12 may be in untreated wet blood form, or alternatively may be treated with a drying agent or fixing agent such as zinc sulfate (FIG. 5). In another alternative, the blood sample 12 may take the form of a dried blood spot.

Figure 3:
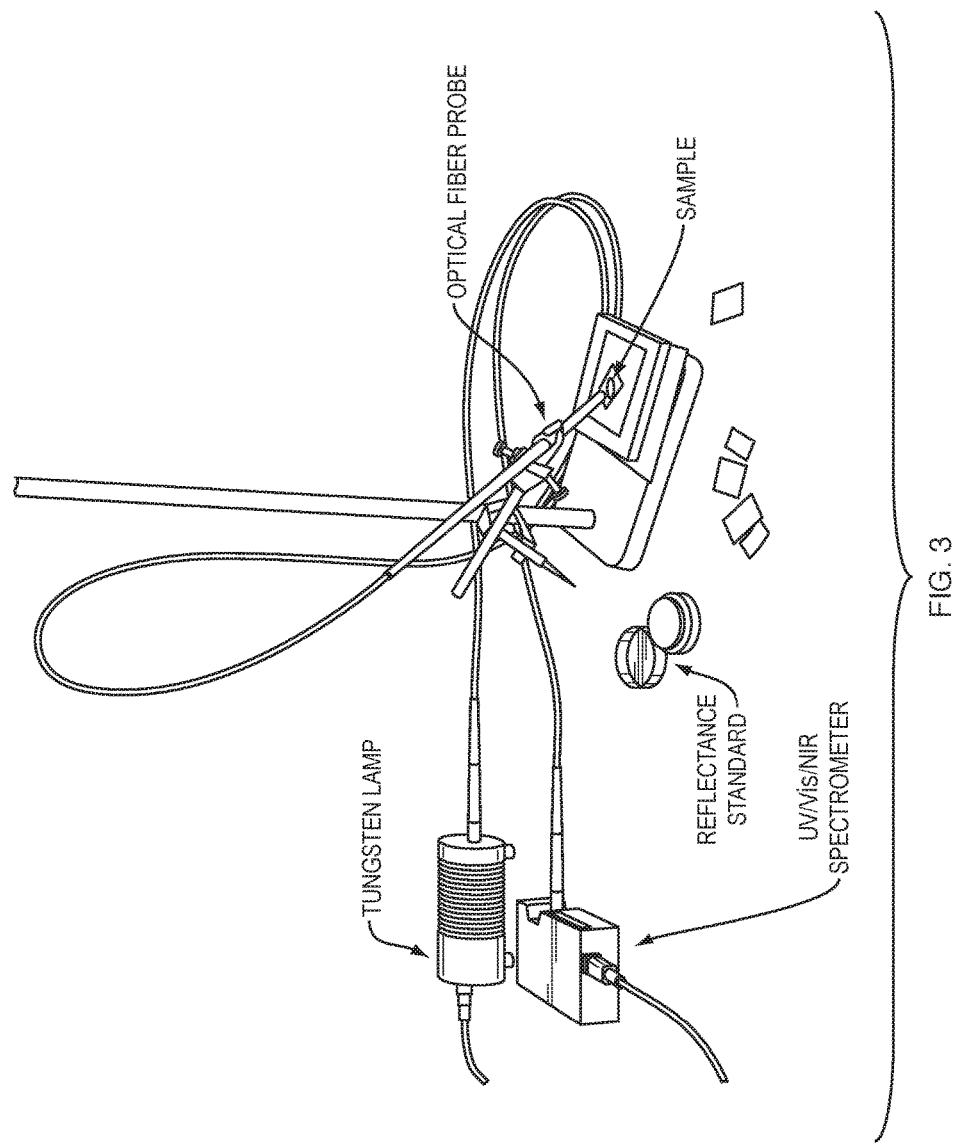
FIG. 3 is showing an experimental system for measuring hematocrit in a whole blood sample, in accordance with one embodiment of the present invention.

The light source 14 is arranged to illuminate the whole blood sample 12 and may be of any type, but should provide illumination in at least two wavelengths of interest, which fall into the range of 400-700 nm and more preferably within the range of about 500-600 nm. The light source or sources 14 may include one or a plurality of devices that emit polychromatic radiation (e.g., an incandescent or discharge lamp) or monochromatic radiation (e.g., a laser or light emitting diode) at the measured wavelengths, and may operate in a continuous manner or intermittent (pulsed) mode. The spectral sensor 13 includes one or a plurality of devices configured to provide measurement of the intensities of light at multiple discrete wavelengths (for instance, at 508 nm, 540 nm, and 561 nm). The spectral sensor may include a grating spectrometer, such as the Czerny-Turner design, or a CCD chip with a filter coating that exposes each sensor cell to a separate wavelength range. The light source 14 and spectral sensor 13 are configured such that the spectral sensor 13 will measure the intensities of light produced by the light source 14 and diffusely reflected by the sample 12. Light source 14 and spectral sensor 13 may be configured using fiber optics (as depicted in FIG. 3, described below), conventional optics, direct mounting of the components, or other practical means. The sample 12 and spectral sensor 13 may be shielded from ambient light by an enclosure 16 or shroud to improve the signal-to-noise ratio of the measured intensity. One or more additional light sources 15 may be used to measure hematocrit using reflectances corresponding to different wavelengths.

When the whole blood sample 12 is illuminated by light from the light source 14, that light is absorbed, diffusely reflected, specularly reflected, or transmitted. Embodiments of the present invention rely on the measurement of diffusely reflected (also called scattered) light. To prevent specular reflections from being detected by the sensor, the spectral sensor 13 and light source 14 should be positioned at an angle to the plane of the substrate, ideally on the same lateral side of the substrate 11 (as referenced to a plane orthogonal to the plane of the substrate 11 and to the plane defined by specular reflection of the light source 14. Spectral sensor 13 and light source 14 are preferably not positioned together normal to the plane of the substrate, or on opposite sides of the plane of the substrate such that the sensor collects light transmitted through the sample and/or substrate. Suitable and unsuitable positioning of the sensor relative to the light source and substrate is illustrated in FIG. 2B.

Collection of the diffusely reflected light may be accomplished, in one embodiment, by employing a fiber optic probe containing multiple fibers, with some coupled to the light source 14, and some connected to the spectral sensor 13. This probe is then mounted at an acute angle to the surface of the substrate 11, positioned such that the blood spot is illuminated by the fibers connected to the light source 14, and some fraction of the diffusely reflected light from the blood spot is captured by the fibers connected to the spectral sensor 13. As such, the scattered or diffusely reflected light does not have to be focused and/or collimated, and no additional optics to control the diffusely reflected light is needed once it is piped back to the spectral sensor 13. The intensity of the diffusely reflected light is recorded in the data system and compared to a reference value obtained using a sample containing no red blood cells. The reference measurement may be performed once and used in multiple analytical measurements, or a separate reference measurement may be taken for each substrate before the application of a blood sample. This approach compensates for any variation in the optical properties of the substrates.

The intensity of the diffusely reflected light is compared to the reference value to generate a reflectance value. In one embodiment, the intensity of the diffusely reflected light collected from the sample 12 is divided by the reference measurement to yield a spectral reflectance, measured as a percent of the reference value. The reflectance is a function of the distance traveled by the light in the sample, the chemical properties of the absorbing species in the sample (i.e., the molar extinction coefficient at each wavelength), and the concentration of the absorbing species in the sample. By employing the same volume of blood and the same type of substrate (e.g., a single grade of filter paper), the path length is held approximately constant. The primary absorbing species in blood at visible wavelengths is hemoglobin, found in red blood cells. The absorbance of light by hemoglobin, therefore, is correlated to the quantity of red blood cells present, and thus to the hematocrit.

The reflected light at any single wavelength can be affected by a variety of factors, including the blood spot size and geometry. In an ideal case, where the light measured is reflected entirely from within the blood spot, a single wavelength measurement may be sufficient to measure hematocrit. However, the spot size and geometry varies with the hematocrit, as high hematocrit samples are substantially more viscous than low hematocrit samples. Thus, it is difficult to ensure that the light being measured is always reflected entirely from within the blood spot. The effect of a smaller than normal blood spot is to increase the overall reflectance, as more lightly-colored substrate is exposed, which reflects light with the same efficiency as the reference sample. The occurrence and extent of this effect is difficult to prevent or predict. To overcome this difficulty, embodiments of the present invention take advantage of the relative changes in reflectance as a function of hematocrit. In low hematocrit samples, several notable peaks and troughs are observed in the reflectance spectrum in the region from 500 nm to 600 nm, as will be explained further in connection with FIGS. 5-7. As the hematocrit increases, these peaks and troughs flatten out relative to each other. For example, by subtracting the reflectance at the bottom of a trough (e.g., 540 nm) from the reflectance at a peak (e.g., 508 nm), a differential reflectance value may be obtained.

A calibration curve may be obtained by applying the measurements using an apparatus arranged in accordance with embodiments of the present invention to whole blood samples with known concentrations of hematocrit. Differential reflectance values at measured wavelengths for samples with known (and varying) amounts of hematocrit are plotted to prepare the calibration curve. In one example, the differential reflectance values may be determined by subtracting the measured reflectance at a first wavelength from the measured reflectance at a second wavelength: DR (differential reflectance)=$R_{\lambda 1}-R_{\lambda 2}$. Other implementations, for example involving pairs of reflectance measurements, to determine the differential reflectance values are possible: $DR=A(R_{\lambda 1}-R_{\lambda 2})+B(R_{\lambda 3}-R_{\lambda 4})$ . . . where A, B, etc., are coefficients determined via a regression analysis or other statistical learning approaches. In yet another example, simple averaging may be used to determine the differential reflectance values: $DR=((R_{\lambda 1}-R_{\lambda 2})+(R_{\lambda 3}-R_{\lambda 4}))/2$. The curve can be fitted to an exponential function.

The controller 17, which may take the form of a general purpose computer or specialized processor or application-specific logic, is configured (e.g., using software instructions) to retrieve the intensity measurements from spectral sensor 13 and determine a differential reflectance value between the reflectance values at the selected wavelengths derived from the intensity measurements. Controller 17 may also be provided with instructions or circuitry for pre-processing the signals received from spectral sensor (e.g., to digitize the signal or for noise reduction), and may be further provided with memory or storage for storing the calibration curves or relationships as well as measurement data. Controller 17 may include or be coupled to a display or output device to present measurement results to an operator. The controller 17 determines the hematocrit level of the whole blood sample based on a stored relationship between hematocrit level and a differential reflectance at the measured wavelengths. The controller 17 compares the calibration data, which may be stored or otherwise represented in memory associated with controller 17 and which relates differential reflectances measurements to known amounts of hematocrit using known samples, to differential reflectance measurements obtained at different wavelengths on the unknown blood samples containing unknown amounts of hematocrit, thus determining the hematocrit level in the unknown whole blood sample using the calibration curve. Additionally, as the spectral sensor 13 may be configured to detect for the intensities of diffusely reflected light at several wavelengths, multiple differential reflectance measurements may be obtained in one spectrum and averaged or subjected to more advanced data analysis to provide improved accuracy for calculating hematocrit. That is to say, the hematocrit values may be calculated from the calibration curves using different wavelength sets (for determining the differential reflectance (DR) values), and then averaging the calculated hematocrit values, such as, for example: $Hematocrit_1=f(DR_1)$, $Hematocrit_2=f(DR_2)$, etc., and then $HCT_{average}=(HCT_1+HCT_2)/2$.

Figure 2A:
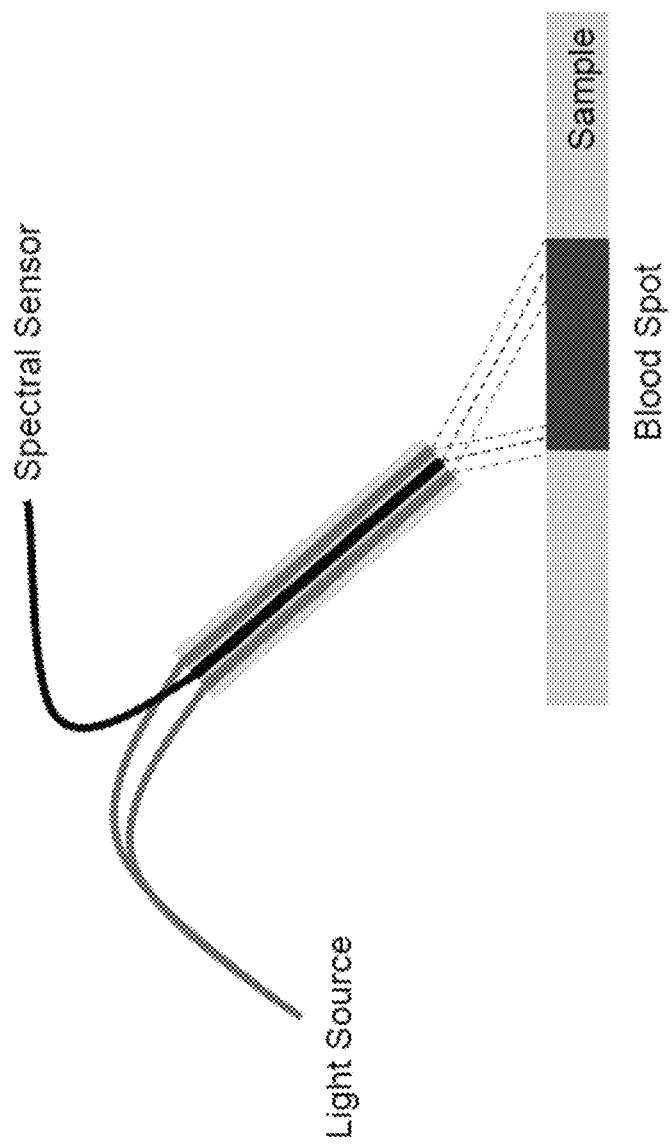
FIG. 2A is block diagram of a system for measuring hematocrit in a whole blood sample, in accordance with one embodiment of the present invention.
Figure 2B:
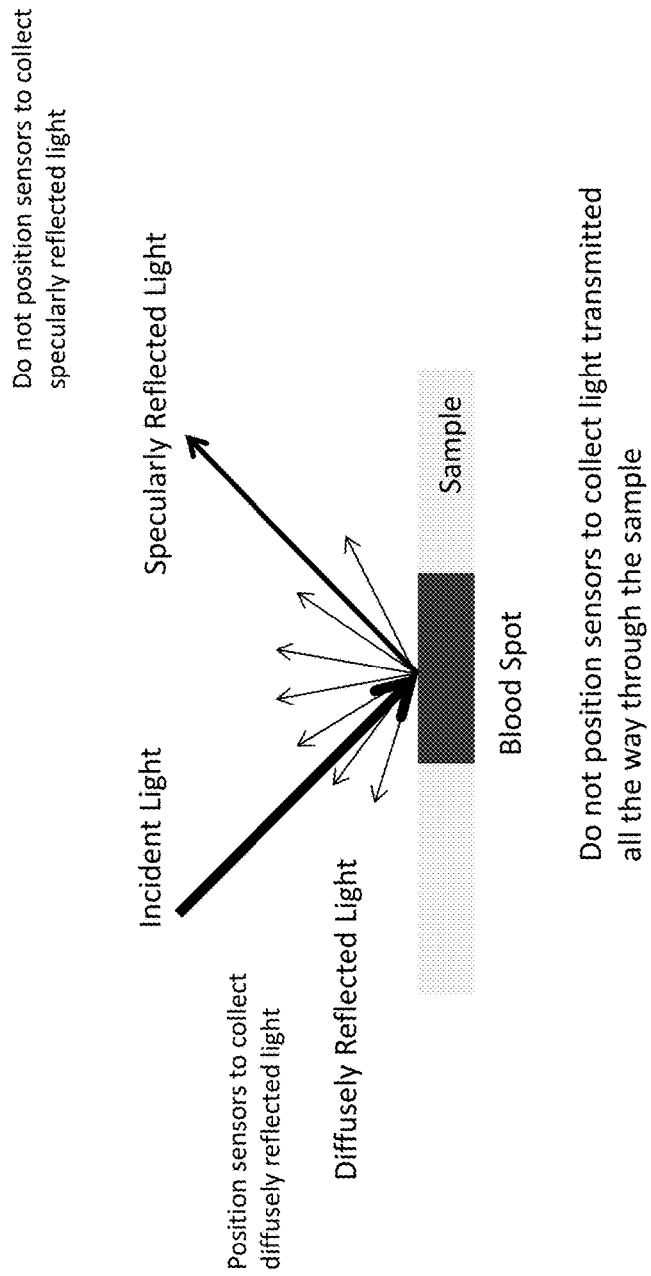
FIG. 2B is a diagram showing the positioning of the spectral sensor relative to the sample and beam direction.

FIG. 2A is block diagram of a system for measuring hematocrit in a whole blood sample, in accordance with one embodiment of the present invention. The light source provides illumination centered on the blood spot of the sample. The spectral sensor measures the light diffusely reflected from the blood spot and is coupled to a controller or a computer having one or more processors and a memory. The embodiment of FIG. 2A utilizes an optical fiber probe with a fiber coupled to the spectral sensor surrounded by fibers which are coupled to the light source. Light is delivered to and collected from the blood spot via the optical fiber probe. The optical fiber probe may be any glass or plastic fiber designed to guide light along its length, is positioned above the sample, and angled or tilted to one side of the sample to avoid detecting specular reflection.

FIG. 3 is showing an experimental system for measuring hematocrit in a whole blood sample, in accordance with one embodiment of the present invention. A tungsten lamp shines light through an optical fiber probe to the sample. Light reflected from the sample is collected by the same optical fiber probe and transmitted to the spectrometer. A UV/Vis/NIR (ultra-violet (UV), visible (Vis) and near infra-red (NIR)) spectrometer may be used to measure the diffusely reflected light. The measured light is compared to reflected light from a reflectance standard and the amount of hematocrit in the whole blood sample is determined therefrom.

Figure 4:
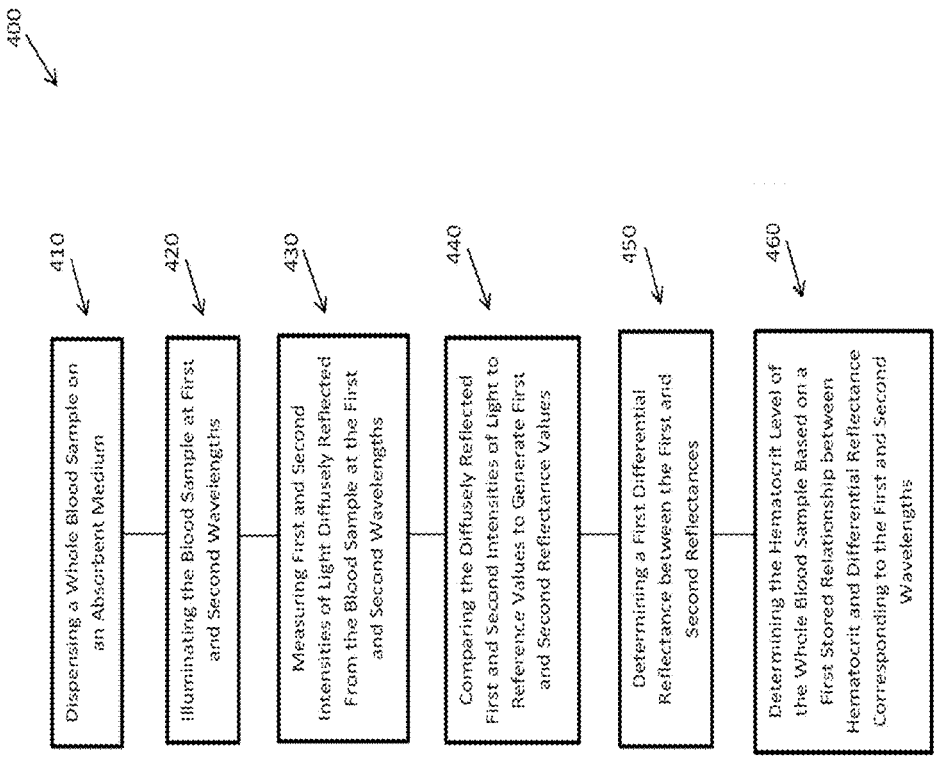
FIG. 4 is a flow chart depicting steps of a method of measuring hematocrit in a whole blood sample, in accordance with one embodiment of the present invention.

FIG. 4 is a flow chart 400 depicting steps of a method of measuring hematocrit in a whole blood sample, in accordance with one embodiment of the present invention. In 410, a whole blood sample is dispensed on an absorbent medium. In one embodiment, the blood sample may be dispensed on the absorbent medium together with an aliquot of the fixing agent zinc sulfate. In 420, the blood sample is illuminated at first and second wavelengths. The first and second wavelengths are different and fall in the range of 400 nm to 700 nm. More preferably, the first and second wavelengths fall in the range of 505 nm to 590 nm. In 430, first and second intensities of light diffusely reflected from the blood sample are measured at the first and second wavelengths, respectively. In 440, the diffusely reflected first and second intensities of light are compared to reference values to generate first and second reflectance values. In 450, a first differential reflectance between the first and second reflectances is determined. In 460, the hematocrit level of the whole blood sample is determined based on stored relationship between the hematocrit level and a differential reflectance corresponding to the first and second wavelengths.

FIG. 5 shows reflectance spectra for whole blood at various levels of hematocrit, produced according to the process shown in FIG. 4. 5 μL of whole blood was deposited onto a paper substrate together with an aliquot of the fixing agent zinc sulfate. The setup that was used to acquire the spectral data was similar to the experimental system depicted in FIG. 3. In this example, the spectrometer measured the reflectances at approximately 508 and 540 nm and subtracted one from the other to generate a differential reflectance measurement, which eliminated the effect of spot geometry variation. It should be noted that LEDs emitting light in this range of wavelengths are readily available.

Figure 6:
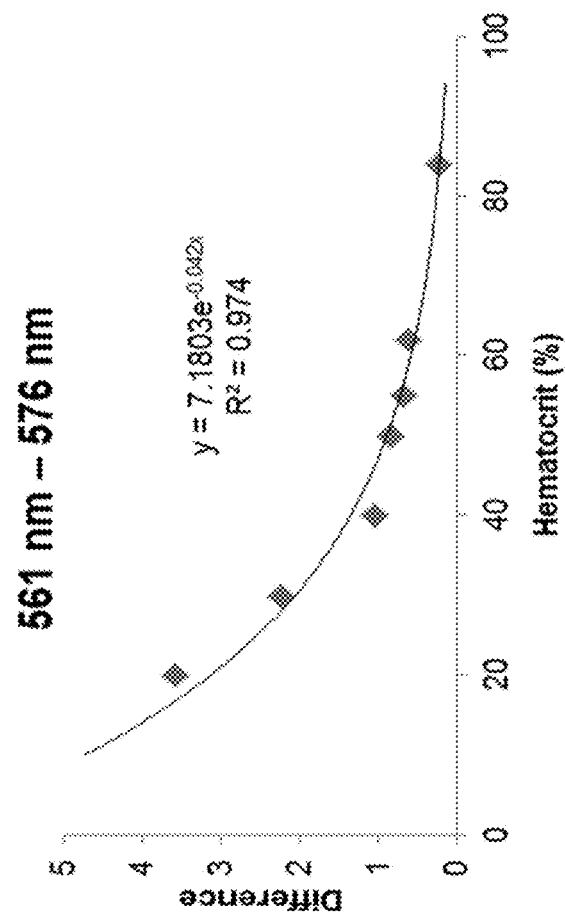
FIG. 6 shows differential values for reflectance at 561 nm minus the reflectance at 576 nm as a function of hematocrit, produced according to the process shown in FIG. 4.

FIG. 6 shows differential values for reflectance at 561 nm minus the reflectance at 576 nm as a function of hematocrit, produced according to the process shown in FIG. 4 using the experimental setup depicted in FIG. 3. The curve shown in FIG. 6 is non-linear and is consistent with the well-known dependence between spot size/shape and hematocrit. The differential reflectance measurement exhibits higher sensitivity at lower hematocrit levels and lower sensitivity at higher hematocrit levels.

Figure 7:
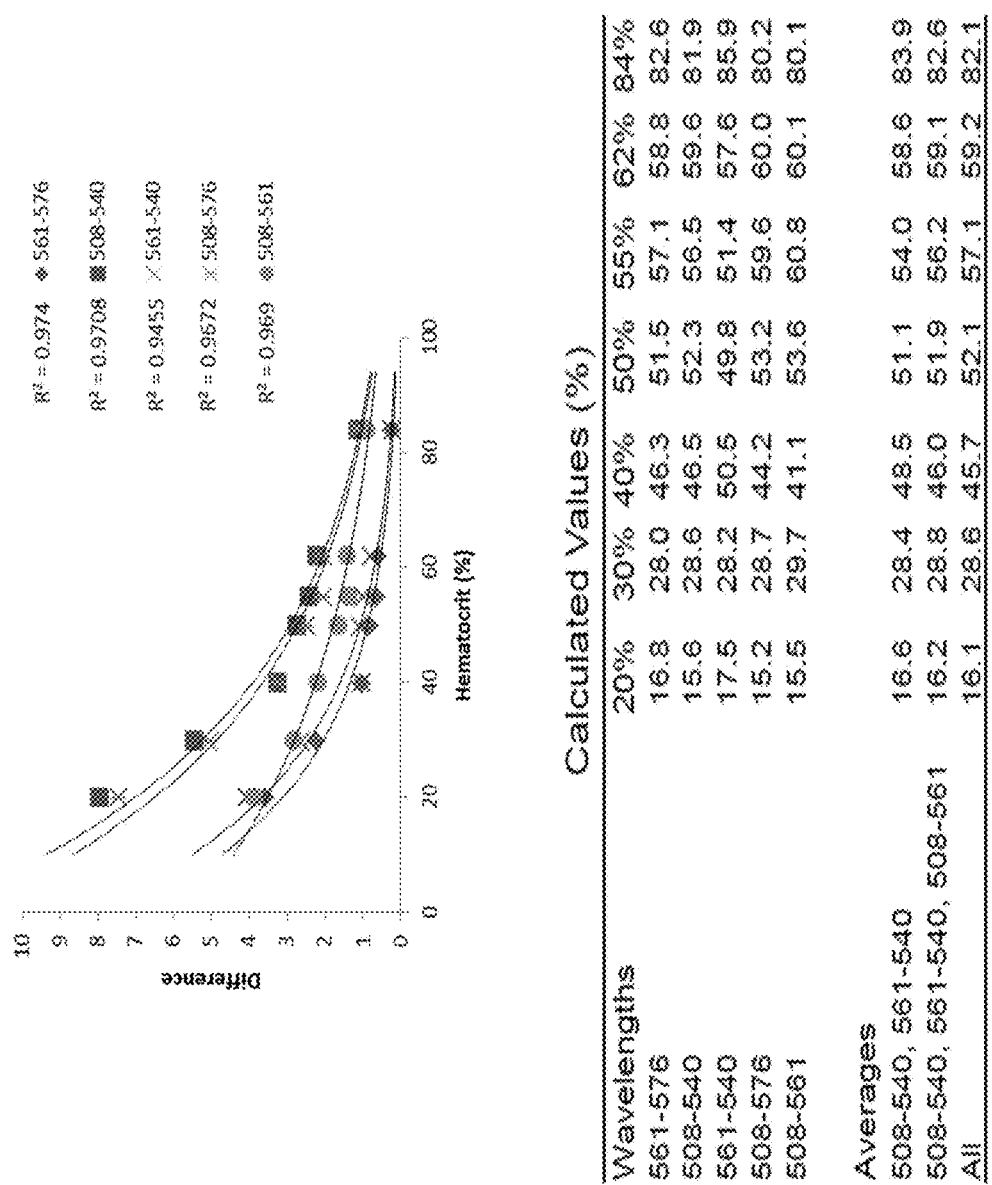
FIG. 7 shows multiple wavelength differential values, produced according to the process shown in FIG. 4.

FIG. 7 shows multiple wavelength differential values, produced according to the process shown in FIG. 4 and the experimental setup of FIG. 3. Differential measurements using multiple combinations of wavelengths were obtained simultaneously. Four different wavelengths (508 nm, 540 nm, 561 nm, and 576 nm) at lower and higher hematocrit levels were used for the differential measurements. As with FIG. 6, the spectra in FIG. 7 show higher sensitivity at lower hematocrit levels and less sensitivity at high hematocrit levels. The table directly below the spectra in FIG. 7 shows calculated values from different pairs of wavelengths as a function of hematocrit. A user provided with this information can select certain combinations of wavelengths that achieve maximum difference and hence improved accuracy.

Embodiments of the present invention include differential reflectance measurement of wet blood spotted on an absorbent medium, blood spotted on an absorbent medium and treated with a drying agent or a fixing agent such as zinc sulfate, and blood spotted on an absorbent medium and dried, such as the dried blood spots used for neonatal screening. Systems and methods of the present invention are also suitable for use as a component of an automated sample preparation system for paper spray or other blood analysis methods, development as a standalone blood spot analyzer for applications with neonatal screening samples, or in blood donation centers. The differential reflectance approach eliminates variability introduced by the differing viscosities of blood samples and possible inconsistencies between paper substrates, which would cause error if a measurement was based solely on one wavelength measurement. Additionally, because the blood is not in contact with the optical system, the methods also minimize the need for cleaning compared to conventional optical hematocrit measurement techniques employing cuvettes or flow cells. When incorporated into a system of the present invention, the advantages of a non-contact approach are particularly relevant as it reduces the cleaning needed between samples and prevents cross-contamination.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

What is claimed is:

1. A system for measuring hematocrit in a whole blood sample deposited on an absorbent substrate, the system comprising:
   a. at least one light source positioned to illuminate the blood sample on the substrate at first and second wavelengths, the first and second wavelengths being different from each other and falling in the range of 400 nm to 700 nm;
   b. a spectral sensor positioned to measure a first intensity and a second intensity of light diffusely reflected from the blood sample at the first and second wavelengths, respectively, wherein the diffusely reflected first and second intensities of light are compared to reference values to generate first and second reflectance values; and
   c. a controller, coupled to the spectral sensor, configured to (i) calculate first and second reflectances from the measured first and second intensities of diffusely reflected light by comparing the first and second intensities to reference values, (ii) determine a first differential reflectance between the first and second reflectances, and (iii) determine the hematocrit level of the whole blood sample based on a first stored relationship between hematocrit level and first differential reflectance corresponding to the first and second wavelengths.

2. The system of claim 1 wherein the at least one light source is further configured to illuminate the blood sample at a third wavelength different from the first and second wavelengths and falling within the range of 400 nm to 700 nm, and the spectral sensor is configured to measure a third intensity of light diffusely reflected from the blood sample at the third wavelength, and wherein the diffusely reflected third intensity of light is converted to a third reflectance value.

3. The system of claim 2 wherein the controller is configured to determine a second differential reflectance between the third reflectance and a selected one of the first and second reflectances, and to determine the hematocrit level based on one or both of the first stored relationship and a second stored relationship between hematocrit level and a differential reflectance corresponding to the third wavelength and the selected one of the first and second wavelengths.

4. The system of claim 1 further comprising a light collector which transmits light from the at least one light source to the blood sample and receives and directs light diffusely reflected from the blood sample to the spectral sensor.

5. The system of claim 4 wherein the light collector is an optical fiber probe having multiple fibers, wherein a first portion of the fibers are coupled to the light source and a second portion of the fibers, different from the first portion, are coupled to the spectral sensor.

6. The system of claim 4 wherein the light collector is mounted at an acute angle to the surface of the substrate.

7. The system of claim 1 wherein the light sources comprise one or more of light emitting diode (LED) sources, laser sources, incandescent lamps, and discharge lamps, or combinations thereof.

8. The system of claim 1 further comprising a housing and a holder for the substrate contained within the housing.

9. The system of claim 1 wherein the absorbent substrate comprises paper.

10. The system of claim 1 wherein the first wavelength and the second wavelength fall in the range of 505 nm to 590 nm.

11. The system of claim 2 wherein the first wavelength, the second wavelength, and the third wavelength fall in the range of 505 nm to 590 nm.

12. A method of measuring hematocrit in a whole blood sample comprising:
   a. dispensing a whole blood sample on an absorbent medium;
   b. illuminating the blood sample at first and second wavelengths, the first and second wavelengths being different from each other and falling in the range of 400 nm to 700 nm;
   c. measuring first and second intensities of light diffusely reflected from the blood sample at the first and second wavelengths, respectively, wherein the diffusely reflected first and second intensities of light are compared to reference values to generate first and second reflectance values; and
   d. determining a first differential reflectance between the first and second reflectances, and determining the hematocrit level of the whole blood sample based on a first stored relationship between hematocrit level and first differential reflectance corresponding to the first and second wavelengths.

13. The method of claim 12 further comprising illuminating the blood sample at a third wavelength different from the first and second wavelengths and falling within the range of 400 nm and 700 nm, and measuring a third intensity of light diffusely reflected from the blood sample at the third wavelength, wherein the diffusely reflected third intensity of light is converted to a third reflectance value.

14. The method of claim 13 further comprising determining a second differential reflectance between the third reflectance and a selected one of the first and second reflectance, and determining the hematocrit level based on one or both of the first stored relationship and a second stored relationship between hematocrit level and a differential reflectance corresponding to the third wavelength and the selected one of the first and second wavelengths.

15. The method of claim 12 wherein the first wavelength and the second wavelength fall in the range of 505 nm to 590 nm.

16. The method of claim 13 wherein the first wavelength, the second wavelength, and the third wavelength fall in the range of 505 nm to 590 nm.

* * * * *